US009299313B2

(12) United States Patent
Goto et al.

(10) Patent No.: US 9,299,313 B2
(45) Date of Patent: Mar. 29, 2016

(54) MEDICAL IMAGE DISPLAY APPARATUS AND PROGRAM

(71) Applicants: Takahiro Goto, Nasushiobara (JP); Shinsuke Tsukagoshi, Nasushiobara (JP)

(72) Inventors: Takahiro Goto, Nasushiobara (JP); Shinsuke Tsukagoshi, Nasushiobara (JP)

(73) Assignees: KABUSHIKI KAISHA TOSHIBA, Tokyo (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 13/680,566

(22) Filed: Nov. 19, 2012

(65) Prior Publication Data

US 2013/0076783 A1 Mar. 28, 2013

Related U.S. Application Data

(63) Continuation of application No. PCT/JP2012/065032, filed on Jun. 12, 2012.

(30) Foreign Application Priority Data

Jun. 14, 2011 (JP) .................................. 2011-132511

(51) Int. Cl.
*G09G 5/00* (2006.01)
*A61B 6/03* (2006.01)
(Continued)

(52) U.S. Cl.
CPC ............... *G09G 5/006* (2013.01); *A61B 6/032* (2013.01); *A61B 6/463* (2013.01); *A61B 6/486* (2013.01); *A61B 6/542* (2013.01); *G06F 3/0481* (2013.01);
(Continued)

(58) Field of Classification Search
None
See application file for complete search history.

(56) References Cited

U.S. PATENT DOCUMENTS 6,546,188 B1 * 4/2003 Ishii et al. ..................... 386/280
7,446,769 B2 * 11/2008 Molander et al. ............. 345/440
(Continued)

FOREIGN PATENT DOCUMENTS

CN 1457745 A 11/2003
CN 101132666 A 2/2008
(Continued)

OTHER PUBLICATIONS

International Search Report mailed Jul. 31, 2012 in PCT/JP2012/065032 filed Jun. 12, 2012.
(Continued)

*Primary Examiner* — Jwalant Amin
(74) *Attorney, Agent, or Firm* — Oblon, McClelland, Maier & Neustadt, L.L.P.

(57) ABSTRACT

According to one embodiment, a medical image display apparatus includes at least a time information obtaining unit, an image storage unit, a display unit, a display unit, and an indicating unit. The time information obtaining unit obtains information on a scan sequence and obtains scan time information as information of a time when a medical image is picked up in accordance with the scan sequence. The image storage unit stores the scan time information in association with the medical image. The display unit simultaneously displays the medical image including the scan time information stored in the image storage unit and a time chart indicating the scan sequence. When a predetermined medical image displayed on the display unit is selected, the indicating unit displays an image indicating a time position on the time chart corresponding to the scan time information included in the medical image.

11 Claims, 10 Drawing Sheets

(51) Int. Cl.
*A61B 6/00* (2006.01)
*G06T 11/60* (2006.01)
*G06T 19/00* (2011.01)
*G06F 9/44* (2006.01)
*G06F 3/0481* (2013.01)
*G06T 11/00* (2006.01)

(52) U.S. Cl.
CPC ............... *G06F 9/4443* (2013.01); *G06T 11/00* (2013.01); *G06T 11/60* (2013.01); *G06T 19/00* (2013.01)

(56) References Cited

U.S. PATENT DOCUMENTS

| | | | | |
|---|---|---|---|---|
| 7,839,420 | B2 * | 11/2010 | Ubillos | 345/619 |
| 2002/0047856 | A1 * | 4/2002 | Baker | 345/700 |
| 2008/0049889 | A1 * | 2/2008 | Tsukagoshi et al. | 378/4 |
| 2009/0028409 | A1 * | 1/2009 | Tsukagoshi et al. | 382/131 |
| 2010/0219074 | A1 * | 9/2010 | Ishibe | 204/406 |

FOREIGN PATENT DOCUMENTS

| | | |
|---|---|---|
| JP | 2008-048956 A | 3/2008 |
| JP | 2008-253569 A | 10/2008 |
| JP | 2009-045445 A | 3/2009 |
| JP | 2010-017215 A | 1/2010 |
| JP | 2010-167254 A | 8/2010 |

OTHER PUBLICATIONS

International Preliminary Report on Patentability with Written Opinion issued on Dec. 17, 2013 in PCT/JP2012/065032(English Translation only).

* cited by examiner

MEDICAL IMAGE DISPLAY APPARATUS AND PROGRAM

CROSS-REFERENCE TO RELATED APPLICATIONS

This application is a Continuation Application of No. PCT/JP2012/065032, filed on Jun. 12, 2012, and the PCT application is based upon and claims the benefit of priority from Japanese Patent Application No. 2011-132511, filed on Jun. 14, 2011, the entire contents of which are incorporated herein by reference.

FIELD

Embodiments described herein relate generally to a medical image display apparatus and a program.

BACKGROUND

An X-ray CT apparatus performs scanning to irradiate a patient's organ region with X-rays in multiple directions and executes image reconstruction processing on the basis of projection data obtained by the X-rays penetrating the organ region in each direction, thereby providing a cross-sectional image of the organ region. Prior to a scan, an operator needs to make a plan for scan conditions and conditions of image reconstruction processing for an organ region and a diagnostic purpose. Such a plan is called "scan plan." Generally, an X-ray CT apparatus provides a user interface environment for a scan plan carried out on an operation console.

A conventional X-ray CT apparatus performs imaging in a Z direction (a body axis direction) within a small range such as 40 mm at a time, so that time-series imaging, i.e., a so-called dynamic scan has been hardly performed. However, in recent years, because multi-detector row X-ray CT apparatuses have become popular, normal imaging and a dynamic scan is increasingly combined. In particular, for example, in multi-slice CT that uses 256 or more rows of flat panel detectors being wide in the slice direction, since the number of scan mode options is very large and imaging speed is considerably high, it is useful to plan more scans such as dynamic imaging, an S & S scan, and a helical scan all in a sequence.

Thus, a scan sequence is displayed so as to provide a user with intuitive understanding of the entire scan sequence including order of scans and scan intervals.

Conventionally, however, images are only displayed on the order of reconstruction in an image confirmation screen that is checked after a scan, and information about time when the images are picked up (hereinafter, referred to as the time information of the image) is not taken into account when the images are displayed. In addition, if obtained images are made into a bundle in a time direction, time information of the images cannot be visually checked.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of a medical image display apparatus and a program according to embodiments of the present invention with reference to the drawings.

In general, according to one embodiment, a medical image display apparatus includes a time information obtaining unit, an image storage unit, a display unit, a display unit, and an indicating unit. The time information obtaining unit obtains information on a scan sequence and obtains scan time information as information of a time when a medical image is picked up in accordance with the scan sequence. The image storage unit stores the scan time information obtained by the time information obtaining unit in association with the medical image. The display unit simultaneously displays the medical image including the scan time information stored in the image storage unit and a time chart indicating the scan sequence. When a predetermined medical image displayed on the display unit is selected, the indicating unit displays an image indicating a time position on the time chart corresponding to the scan time information included in the medical image.

First Embodiment

A medical image display apparatus according to a first embodiment treats information in which medical images picked up in accordance with a scan sequence are associated with times when the medical images are picked up. In the following description, as the medical image display apparatus according to the present embodiment, an X-ray CT apparatus is used by way of example.

Figure 1:
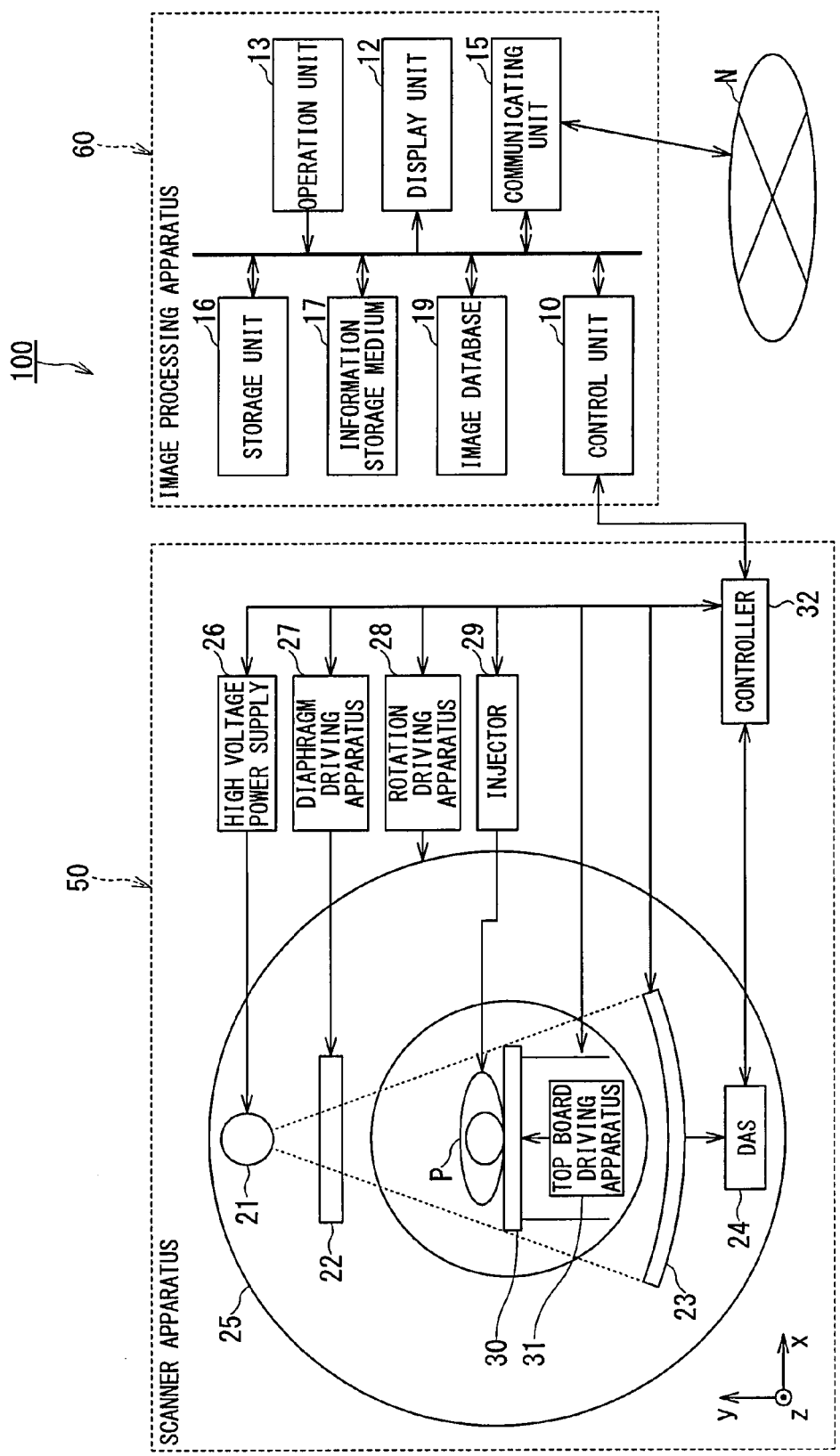
FIG. 1 is a block diagram illustrating a schematic configuration of an X-ray CT apparatus according to an embodiment of the present invention.
Figure 2:
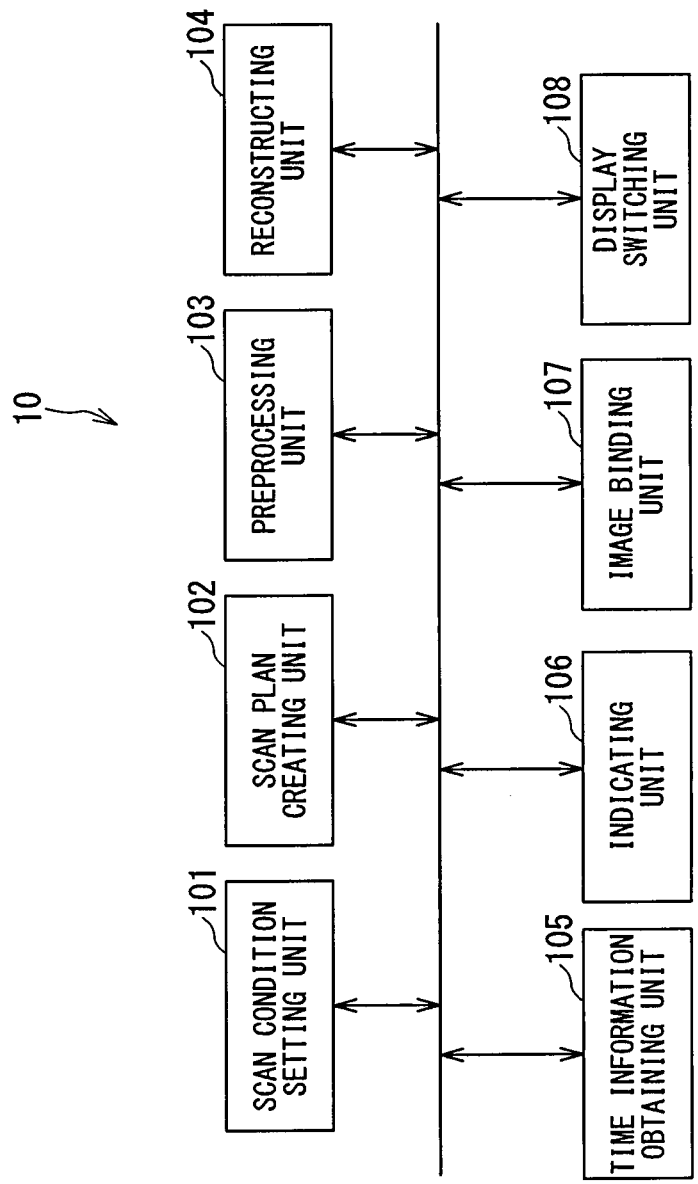
FIG. 2 is a block diagram illustrating a detail of a control unit.

FIG. 1 is a block diagram illustrating a schematic configuration of an X-ray CT apparatus 100 according to an embodiment of the present invention. The X-ray CT apparatus 100 mainly includes a scanner apparatus 50 and an image processing apparatus 60. The scanner apparatus 50 of the X-ray CT apparatus 100 is typically installed in an examination room and configured to generate X-ray transmission data on an area of an object P. On the other hand, the image processing apparatus 60 is typically installed in a control room adjacent to the examination room and configured to generate projection data on the basis of the transmission data to generate and display a reconstruction image.

The scanner apparatus 50 includes an X-ray tube (X radiation source) 21, a diaphragm 22, an X-ray detector 23, a DAS (data acquisition system) 24, a rotation portion 25, a high voltage power supply 26, a diaphragm driving apparatus 27, a rotation driving apparatus 28, an injector (contrast medium agent injecting apparatus) 29, a top board 30, a top board driving apparatus 31, and a controller 32.

The X-ray tube 21 causes an electron beam to collide with a metal target in response to a tube voltage supplied from the high voltage power supply 26 to generate bremsstrahlung X-rays, and applies the X-rays to the X-ray detector 23. Fan beam X-rays and cone beam X-rays are formed by the X-rays applied from the X-ray tube 21. The X-ray tube 21 is supplied with power required to apply X-rays in response to control of the controller 32 through the high voltage power supply 26.

The diaphragm driving apparatus 27 causes the diaphragm 22 to adjust an area to be irradiated by the X-ray tube 21 with X-rays in a slice direction. That is, the diaphragm driving apparatus 27 is allowed to adjust an aperture of the diaphragm 22 to change the area irradiated with X-rays in the slice direction.

The X-ray detector 23 is a one-dimensional array type X-ray detector 23 (also referred to as a single-slice type detector) having a plurality of channels arranged in a channel (CH) direction and a single row of X-ray detecting elements (charge storage elements) arranged in the slice direction. Alternatively, the X-ray detector 23 is a matrix-formed X-ray detector 23, namely, a two-dimensional array type detector (also referred to as a multi-slice type sensor) having a plurality of channels in the channel direction (CH) and a plurality of rows of X-ray detecting elements in the slice direction. The X-ray detecting elements of the X-ray detector 23 senses X-rays applied from the X-ray tube 21.

The DAS 24 amplifies signals of transmission data sensed by each X-ray detecting element of the X-ray detector 23 and converts the signals into digital signals. Output data from the DAS 24 is supplied to the image processing apparatus 60 through the controller 32 of the scanner apparatus 50.

The rotation portion 25 holds the X-ray tube 21, the diaphragm 22, the X-ray detector 23, and the DAS 24 as an integrated unit. The rotation portion 25 can rotate about the object P with the X-ray tube 21, the diaphragm 22, the X-ray detector 23, and the DAS 24 being an integrated unit and with the X-ray tube 21 and the X-ray detector 23 opposing each other. It is assumed that a direction parallel to an axis of rotation of the rotation portion 25 is defined as a z axis direction, and a plane orthogonal to the z axis direction is defined with an x axis direction and a y axis direction.

The high voltage power supply 26 supplies the X-ray tube 21 with power required to apply X-rays in response to control of the controller 32.

The diaphragm driving apparatus 27 has a mechanism that allows, in response to control of the controller 32, the diaphragm 22 to adjust an area to be irradiated with X-rays in the slice direction.

The rotation driving apparatus 28 has a mechanism that allows, in response to control of the controller 32, the rotation portion 25 to rotate about a cavity space with a positional relationship of the rotation portion 25 maintained.

The injector 29 is an apparatus that, in response to control of the controller 32, injects a contrast medium agent in a catheter (a catheter tube, not shown) that is inserted in an affected area of the object P.

The top board 30 is a bed on which the object P can be placed. The top board driving apparatus 31 has a mechanism that, in response to control of the controller 32, moves the top board 30 up and down along the y axis as well as backward and forward along the z axis. The rotation portion 25 has an opening in a central portion. The object P who is placed on the top board 30 at the opening space is put into the opening.

The controller 32 controls the X-ray detector 23, the DAS 24, the high voltage power supply 26, the diaphragm driving apparatus 27, the rotation driving apparatus 28, the injector 29, and the top board driving apparatus 31 to perform a scan.

The image processing apparatus 60 has a computer-based configuration and includes a control unit 10, a display unit 12, an operation unit 13, a communicating unit 15, a storage unit 16, an information storage medium 17, and an image database 19. These units are allowed to communicate with each other via a bus. The control unit 10 of the image processing apparatus 60 is connected to the controller 32 of the scanner apparatus 50 and controls the operations of both of the apparatuses. Also, the image processing apparatus 60 is capable of communicating with an external device via a network N such as a backbone LAN (local area network) in a hospital.

The operation unit 13 may be a keyboard or a mouse and is used to input data. Also, the operation unit 13 issues an instruction to perform operations of mechanisms in the scanner apparatus 50 via the controller 32. The communicating unit 15 is connected to the LAN in the hospital to communicate with an external device.

The display unit 12 may be a monitor. The display unit 12 combines projection image data generated by the control unit 10 with examination information (characters and scales of parameters) such as a patient name into signals, D/A-converts the resultant signals, and displays the converted signals as video signals. Examples of the display unit 12 include a reference monitor for displaying a projection image output from the control unit 10, as a still image and a system monitor for chiefly displaying data used to control the scanner apparatus 50, such as data for changing FOV (field of view).

Also, as a confirmation screen to be checked after a scan, the display unit 12 displays tomogram data and a scan sequence created with a scan plan creating unit 102 described later at the same time.

The storage unit 16 is a work area for the control unit 10 and the communicating unit 15, and may be provided by RAM (Random Access Memory).

The information storage medium 17 (a computer-readable medium) is storage of a program and data. The information storage medium 17 may be provided by a hard disk drive or memory (Flash Memory, ROM: Read Only Memory). In the information storage medium 17, applications and a program for causing a computer to function as portions in the present embodiment (a program for causing a computer to execute processing of each portion) are stored.

The control unit 10 controls the entire apparatus. The control unit 10 is an arithmetic unit that executes a variety of arithmetic and control processes. Functions of the control unit 10 may be provided by a program or hardware such as processors (e.g., a CPU and a DSP) and an ASIC (e.g., a gate array). The control unit 10 performs a variety of processes in the present embodiment on the basis of the program (data) stored in the information storage medium 17.

The control unit 10 includes a scan condition setting unit 101, the scan plan creating unit 102, a preprocessing unit 103, a reconstructing unit 104, a time information obtaining unit 105, an indicating unit 106, an image binding unit 107, and a display switching unit 108.

The scan condition setting unit 101 sets scan conditions of an object. The scan conditions include a very large number of set items such as a scan mode for indicating a scan type, a tube voltage, a tube current, a diameter of imaging field of view (S-FOV), a diameter of reconstruction field of view (D-FOV), a slice thickness of imaging, a slice thickness of reconstruction, a helical pitch, the number of slice images, a start time representing a time period elapsed from the start of scan, a wait time representing a time interval between adjacent scan elements, and a rest time representing a time interval between X-ray generations in a scan element in, for example, an S & S mode. Typically, the scan mode includes scanogram imaging, a dynamic scan, an S & S scan, and a helical scan.

The scan plan creating unit 102 creates, as a scan plan, a scan sequence in which the object P is scanned under the scan conditions set by the scan condition setting unit 101. The plan is created with a time chart of changes in dose, for example. A detail thereof will be described later.

The preprocessing unit 103 generates projection data by performing preprocessing such as logarithmic transformation processing and correction processing, including sensitivity correction, on raw data (scan data) output from the DAS 24 of the scanner apparatus 50 via the controller 32.

The reconstructing unit 104 performs reconstruction processing such as a fan beam reconstruction scheme or a cone beam reconstruction scheme on the projection data generated by the preprocessing unit 103 to generate (or reconstruct) slice tomogram data and stores thin slices of tomogram data taken at one scan as one stack in the image database 19.

The time information obtaining unit 105 obtains scan sequence information from the scan plan creating unit 102. Also, the time information obtaining unit 105 obtains scan time information in scan data output from the DAS 24 of the scanner apparatus 50 and stores the time information with corresponding tomogram data in the image database 19.

The indicating unit 106 displays, on the basis of the time information corresponding to predetermined tomogram data, obtained by the time information obtaining unit 105 and stored in the image database 19, an image such as a display bar indicating a particular position in the time chart of changes in dose being the scan sequence displayed on the display unit 12. Also, the indicating unit 106 indicates a particular position in the scan sequence at which tomogram data is not created. A detail thereof will be described later.

The image binding unit 107 binds a plurality of stacks of tomogram data having the same scan conditions set by the scan condition setting unit 101 and consecutive scan times into one stack. In the bound stack, pieces of time information of the stacks are added together.

The display switching unit 108 switches, for one stack into which the image binding unit 107 has bound a plurality of stacks of tomogram data, between presence and absence of display of the time chart based on the scan time information in each stack. A detail thereof will be described later.

In the image database 19, tomogram data in one scan reconstructed by the reconstructing unit 104 is stored as one stack. Also, in the image database 19, the scan time information obtained by the time information obtaining unit 105 is stored with corresponding tomogram data.

Figure 3:
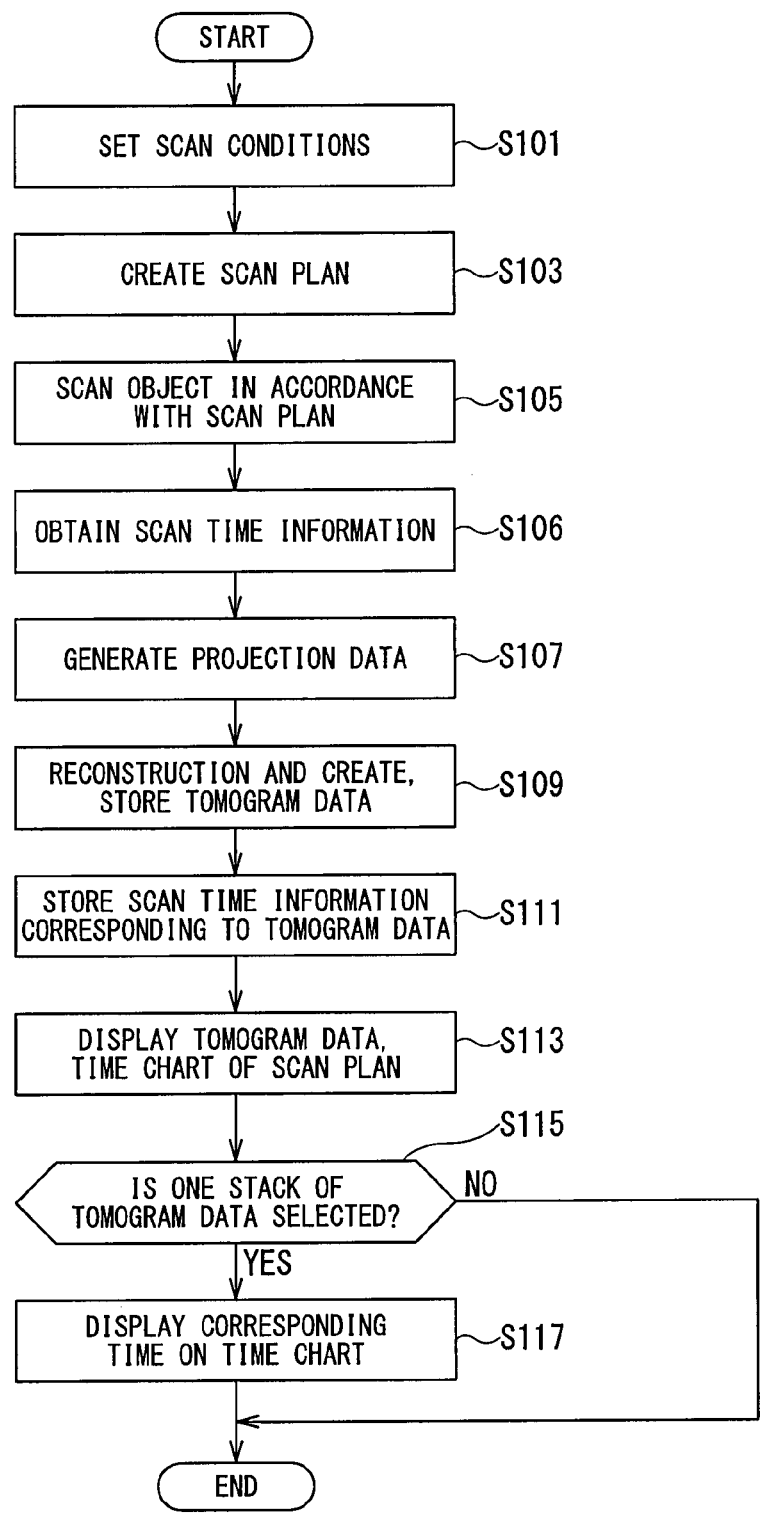
FIG. 3 is a flow chart illustrating an exemplary operation of an X-ray CT apparatus according to a first embodiment.

Now, an operation of the X-ray CT apparatus 100 having such a configuration will be described with reference to the flow chart in FIG. 3.

The scan condition setting unit 101 sets various conditions such as a scan mode, a tube voltage, and a slice thickness for scanning the object P (step S101). Then, as a scan plan, the scan plan creating unit 102 creates a scan sequence for the object P under the various scan condition set by the scan condition setting unit 101 in step S101 with a time chart of changes in dose (step S103).

Figure 4:
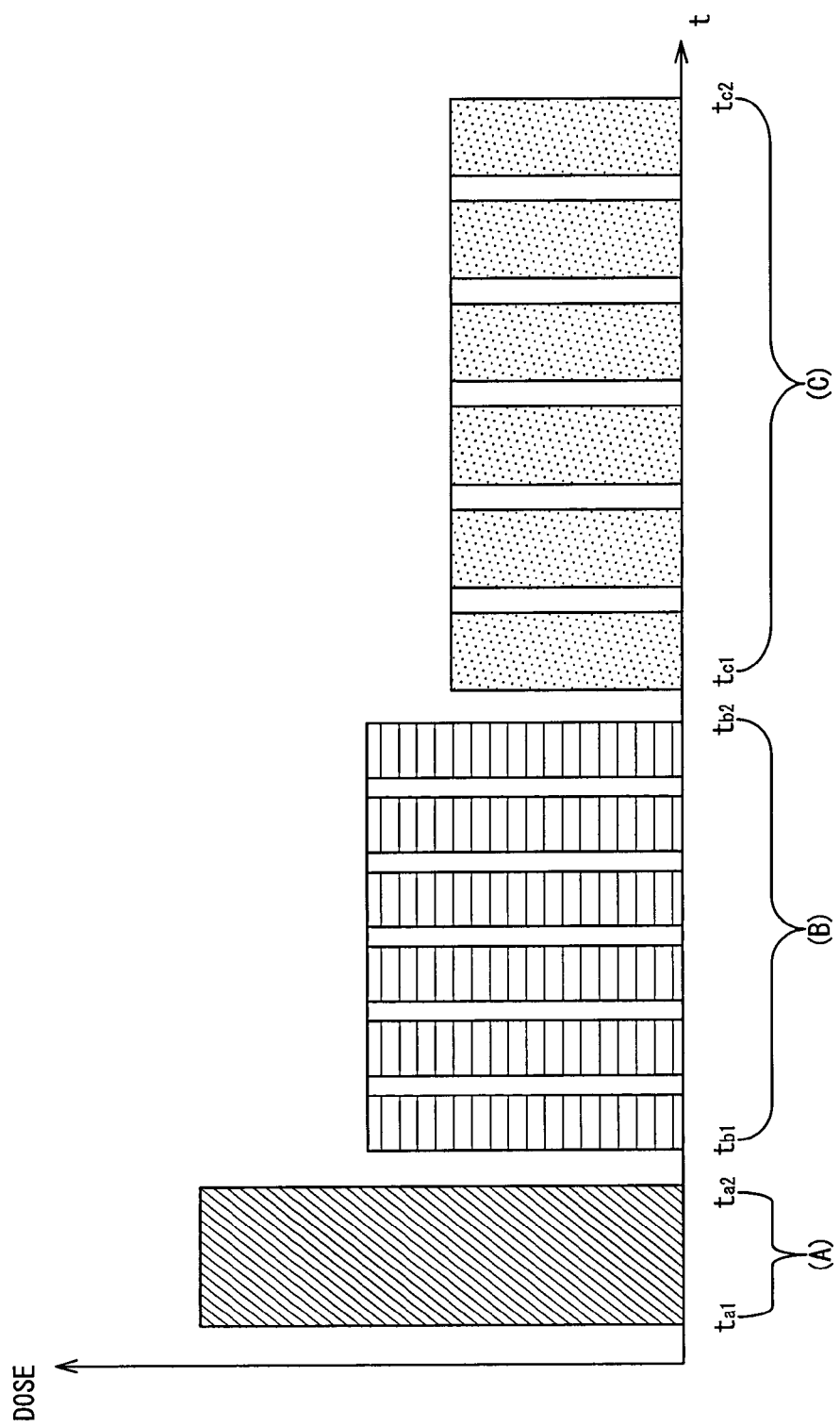
FIG. 4 illustrates an exemplary time chart of changes in dose in a scan plan.

FIG. 4 illustrates an exemplary time chart of changes in dose in a scan plan. A part (A) indicates a time $t_{a1}$ to $t_{a2}$ when sequential scans are performed and a dose. Toward achieving maximum possible control of the object P's exposure, the scan plan in the sequential scans of the part (A) is established so that the scans are completed in a short period of time even if a dose is large.

A part (B) indicates a time $t_{b1}$ to $t_{b2}$ when intermittent scans are performed at short intervals and a dose. In the part (B), since six scans are performed during the time $t_{b1}$ to $t_{b2}$, a dose per scan is smaller than that of sequential scans in the part (A). Also, the plan is made so that a time of each scan is short and a total time of the six scans is longer than the time of the part (A).

A part (C) indicates a time $t_{c1}$ to $t_{c2}$ when intermittent scans are performed at intervals longer than the time of the part (B) and a dose. In the part (C), since scans are performed six times during the time longer than that of the part (B), a dose per scan is smaller than that of the part (B). The plan is made so that a time of each scan is longer than that of the part (B), and a total time of the six scans is also longer than that of the part (B).

It should be noted that a vertical axis shows tube currents in FIG. 4, but another indicator indicating dose may also be adopted.

Referring back to FIG. 3, the control unit 10 then controls an operation of the scanner apparatus 50 through the controller 32 to scan the object P in accordance with the scan plan created in step S103 (step S105) and collect scan data (raw data) output from the DAS 24 via the controller 32. At this time, the time information obtaining unit 105 obtains scan time information on the scan data (step S106).

Then, the preprocessing unit 103 performs logarithmic transformation processing and correction processing on the raw data collected in step S105 to generate projection data (step S107). Then, the reconstructing unit 104 performs reconstruction processing on the projection data generated by the preprocessing unit 103 in step S107 to create slice tomogram data and stores a plurality of thin slices of tomogram data per scan as one stack in the image database 19 (step S109).

Next, the time information obtaining unit 105 obtains information on the time chart indicating the scan sequence of the scan plan created in step S103. Also, the scan time information obtained in step S106 is stored in association with the tomogram data stored in the image database 19 in step S109 (step S111).

Then, the display unit 12 simultaneously displays, on a confirmation screen viewed after the scan, both of the tomogram data including the scan time information stored in the image database 19 in step S111 and the time chart of the scan plan (step S113). At this time, the tomogram data is displayed as stacks on a one-by-one basis. If one stack of the tomogram data displayed on the display unit 12 is selected through the operation unit 13 (step S115: Yes), then the indicating unit 106 indicates a corresponding position on the time chart with a dotted display bar, based on the time information in this tomogram data (step S117).

Figure 5:
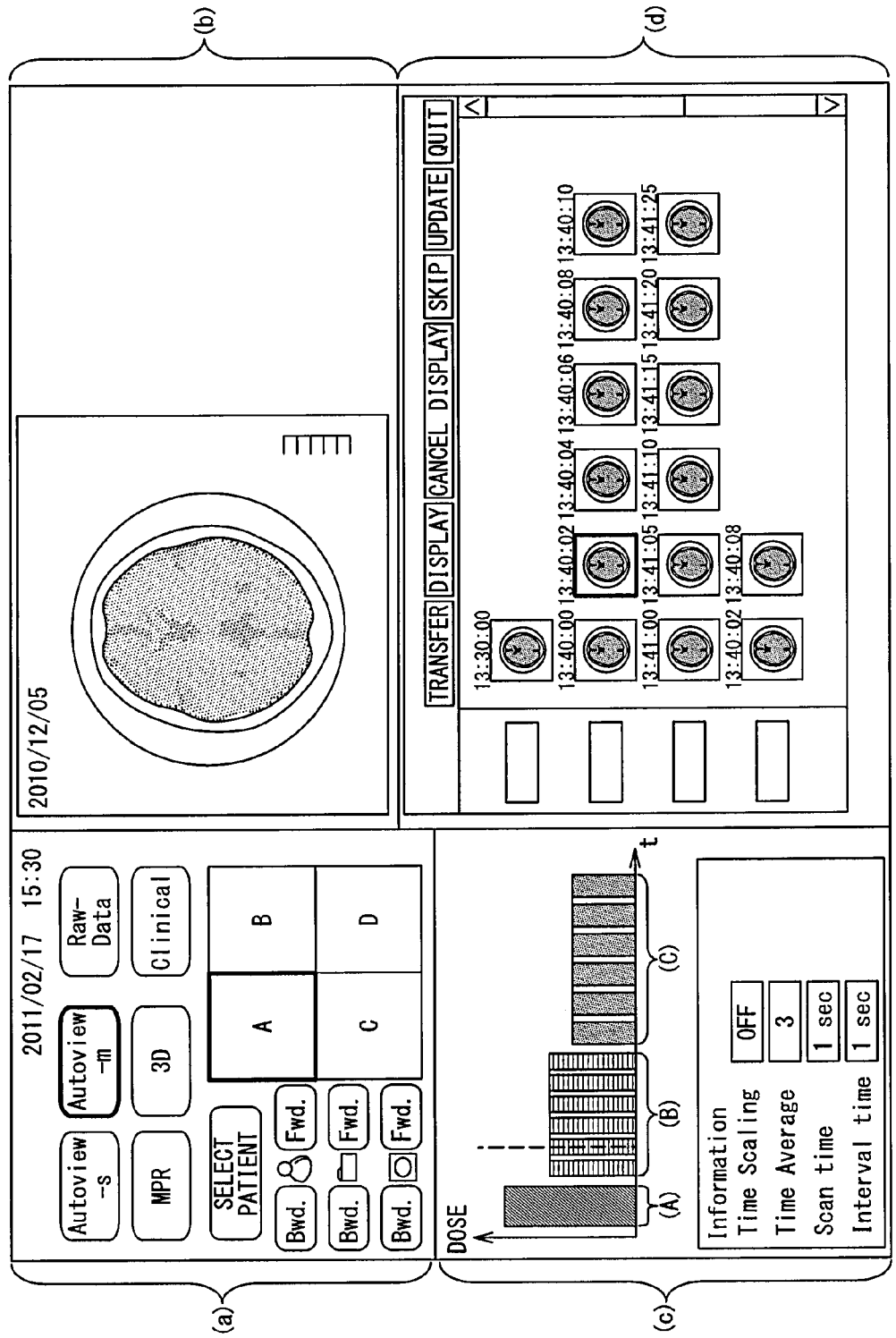
FIG. 5 illustrates an exemplary confirmation screen including bound stacks.

FIG. 5 illustrates an exemplary confirmation screen displayed on the display unit 12. An upper left area (a) in the screen shows display buttons, a patient selection button, and which of images A, B, C, and D from modalities is being viewed in detail. The images are displayed on four sections into which a screen is divided. In FIG. 5, a detail of the image A surrounded by a solid frame is being displayed. An upper right area (b) in the screen displays a CT image of a brain, and a lower right area (d) displays, for each stack, tomogram data slices including the CT images of the brain in the area (b). A lower left area (c) shows the time chart of the changes in dose shown in FIG. 4 in the scan plan and detailed information on the scan.

The area (d) in FIG. 5 displays the stacks of the tomogram data according to the scan plan displayed on the area (c) (FIG. 4). The stacks of the tomogram data are displayed with scan times; for example, the scan times are superimposed on the data. At a first row of the area (d), a stack of the tomogram data obtained at the time of the sequential scans in FIG. 4(A) is displayed. At a second row, stacks of the tomogram data at the time of the intermittent scans at short intervals in FIG. 4(B) are displayed. At this time, since the scans are performed six times, the number of stacks is six. At a third row, stacks of the tomogram data obtained at the time of the intermittent scans at long intervals in FIG. 4(C) are displayed. Since the scans this time are also performed six times, the number of stacks is six.

For example, if a second stack at the second row is selected in the area (d) of FIG. 5, then in the time chart displayed on the area (c), a dotted display bar is displayed at a position of time when the selected stack is scanned (in this example, the second position in the short-interval intermittent scans (B)).

Also, the image binding unit 107 may bind a plurality of stacks having same scan conditions and consecutive scan times into one stack (bound stack) and display the bound stack on the area (d) (see FIG. 5). Binding a plurality of stacks reduces noise in an image itself and results in a clear image of inflow and outflow in blood vessels, for example.

Fourth or later rows of the area (d) display tomogram data obtained by binding for each row or reconstructing the tomogram data in the first to third rows. In FIG. 5, by way of example, the image binding unit 107 binds, every three stacks starting from the top of the tomogram data items at the second row obtained by the consecutive scans, the data items into one in a time direction, and the bound stacks are displayed at the fourth row.

In the area (d), for example, if any tomogram data is reconstructed, the tomogram data is displayed at a lower row in creation order regardless of scan times of the original tomogram data. Also if a stack of the reconstructed tomogram data is selected, a position of a corresponding scan time in the time chart displayed in the area (c) is indicated by a display bar.

Thus, even if tomogram data items are not arranged in the order of scan times in the area (d), the operator can readily judge at which scan time on the time chart in the area (c) a particular tomogram data item is.

If one bound stack made of a plurality of stacks is selected, a time period of a plurality of scan sequences corresponding to the stacks configuring the bound stack may be displayed on the time chart of the area (c). An example of this case is shown in the area (c) of FIG. 6.

Figure 6:
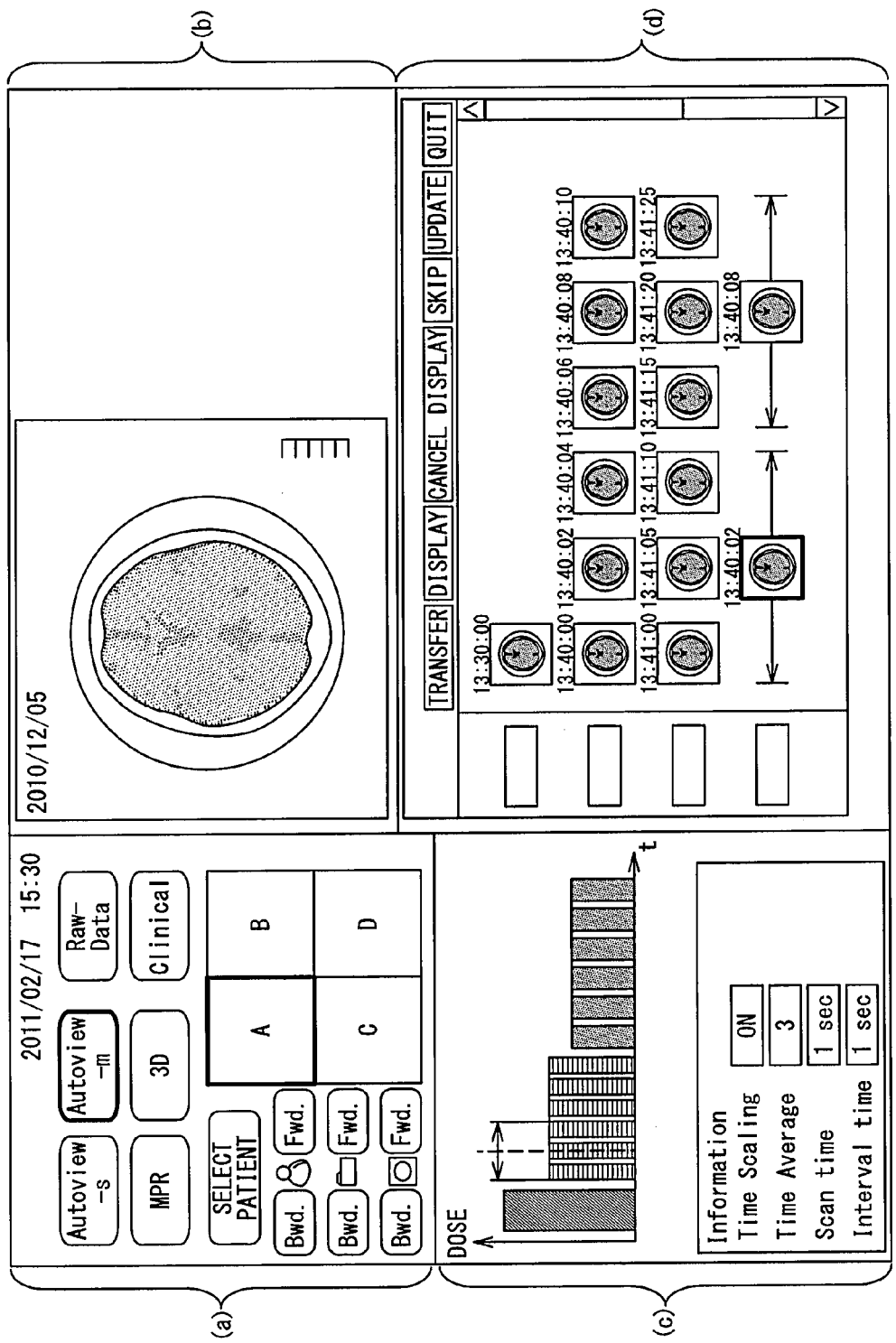
FIG. 6 illustrates an exemplary confirmation screen including time-scale display of the bound stacks.

Also, the display switching unit 108 may display with a time-scale a bound stack made by binding tomogram data items in the area (d). The area (d) in FIG. 6 shows an exemplary confirmation screen in which the time-scale display is performed. Similarly to FIG. 5, at the fourth row of area (d) in FIG. 6, the tomogram data items are sequentially bound into each stack every three stacks starting from a top of the data items at the second row. Each stack at the fourth row is displayed with a time-scale in which pieces of time information of three stacks configuring each bound stack are added together. At this time, in detailed information on the scan in the area (c), time-scale display is "ON." Also, the display switching unit 108 may switch between presence and absence of the time-scale display and display a current state on the confirmation screen.

Note that the time-scale display is defined as displaying a bound stack in connection with an image (see arrow images in FIG. 5) indicating a period during which medical images configuring the bound stack are picked up at the time of displaying the bound stack.

The tomogram data at the fourth row in the area (d) indicates that corresponding three stacks of the tomogram data at the second row are bound, and includes three-stack time information. According to the time-scale display, a time period corresponding to bound tomogram data is displayed under the tomogram data at the second row, and thereby the operator can visually confirm stacked images and a time range of images on the area (d).

It should be noted that a bound stack may be displayed at the bottom row as shown in the area (d) of FIG. 5, or may be displayed at an upper or a lower row adjacent to a row at which a plurality of stacks configuring the bound stack are displayed. For example, assume that a plurality of stacks at the second row are bound to generate a bound stack. In this case, this bound stack may be displayed at the third row immediately under the second row, and tomogram data items originally at the third or later rows may be each moved down by one row. Alternately, this bound stack may be displayed at the second row, and tomogram data items originally at the second or later rows may be each moved down by one row.

Figure 7:
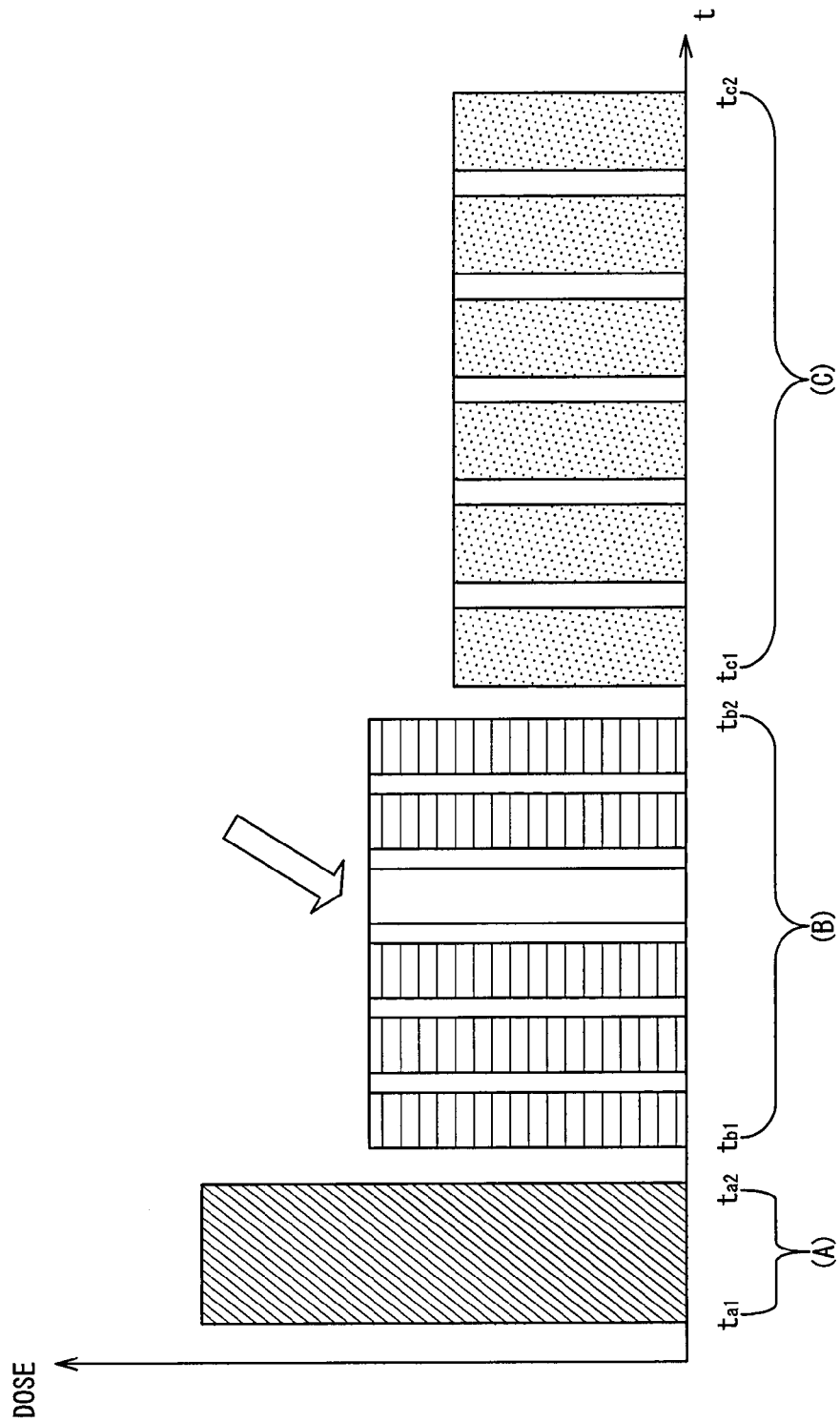
FIG. 7 illustrates an exemplary time chart of changes in dose in a scan plan occurring if a subject body moves.

When a scan is performed in accordance with the scan plan in FIG. 4, if generated tomogram data cannot be used because of high noise caused by body movements of the object P, the indicating unit 106 may indicate a part of the body movements on the time chart displayed in the area (c) of FIG. 5 or FIG. 6. A display example of the time chart in this case is shown in FIG. 7. In FIG. 7, suppose that a body movement of the object P occurs at the fourth one of the intermittent scans in the part (B). At this time, even if the reconstructing unit 104 attempts to create tomogram data, since discontiguous slices of data would be combined with each other at the body movement part, a stack cannot be generated. As a result, fourth tomogram data is not created. Eventually, the number of tomogram data would be reduced by one, resulting in only five. Then, the indicating unit 106 indicates a scan sequence of the body movement part on the time chart. In FIG. 7, the fourth scan sequence in the intermittent scans (B) is indicated by an arrow.

Thus, even if tomogram data is not displayed in the area (d), because the time chart in the area (c) can indicate which of scans has been deleted due to a problem, the operator can visually make a judgment.

According to the X-ray CT apparatus 100 of the present embodiment, a scan plan is created as a scan sequence, and a scan is performed in accordance with the scan plan to obtain tomogram data. Further, corresponding scan time information is obtained and stored. After the scan, a confirmation screen simultaneously displays both of the tomogram data and the scan sequence and also displays a scan time corresponding to predetermined tomogram data on the scan sequence. Accordingly, the operator can visually confirm time information on an image collected by a scan. Therefore, according to the X-ray CT apparatus 100 of the present embodiment, the operator can intuitively understand time information on an image obtained after a scan.

Second Embodiment

Next, a medical image display apparatus of a second embodiment according to the present invention will be described.

The medical image display apparatus according to the second embodiment treats information having medical images associated with times when the medical images are picked up.

In the following description, as the medical image display apparatus according to the present embodiment, the same X-ray CT apparatus 100 as that in the first embodiment is used by way of example.

The X-ray CT apparatus 100 in the second embodiment is different from the X-ray CT apparatus 100 in the first embodiment in that information on a scan sequence is not necessary and additionally used. Because other components and operations are substantially the same as those of the X-ray CT apparatus 100 illustrated in FIG. 1, the same reference numerals are assigned to the same components and a description thereof will be omitted.

Figure 8:
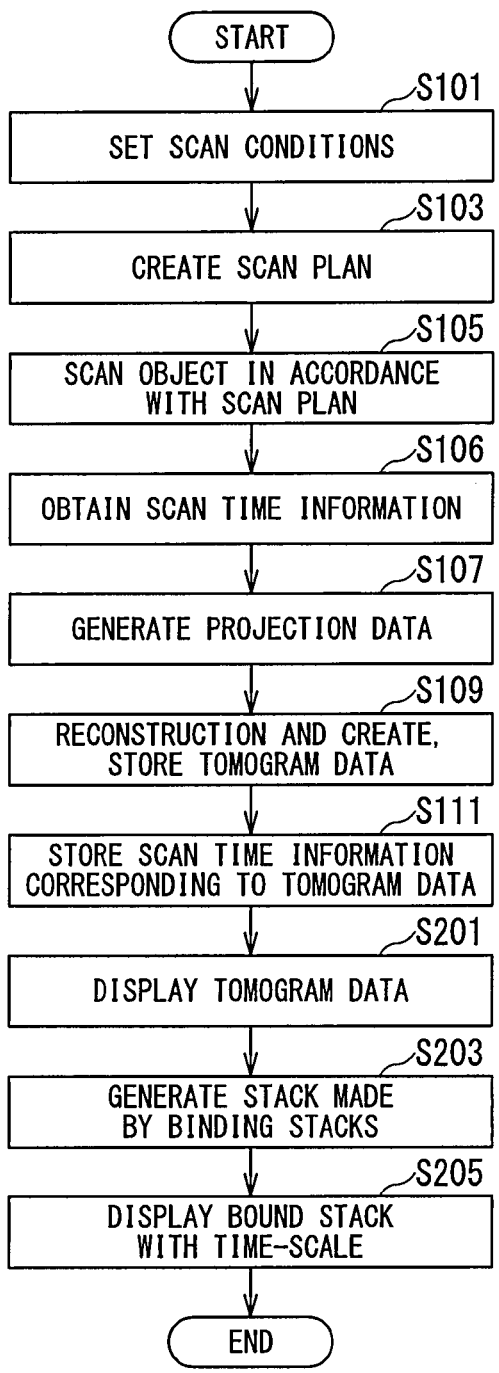
FIG. 8 is a flow chart illustrating an exemplary operation of an X-ray CT apparatus according to a second embodiment.

FIG. 8 is a flow chart illustrating an exemplary operation of the X-ray CT apparatus 100 according to the second embodiment. Same reference numerals are assigned to the same steps as those in FIG. 3, and a redundant description thereof is omitted.

In step S201, the display unit 12 displays tomogram data including scan time information stored in the image database 19 on a confirmation screen seen after a scan.

Figure 9:
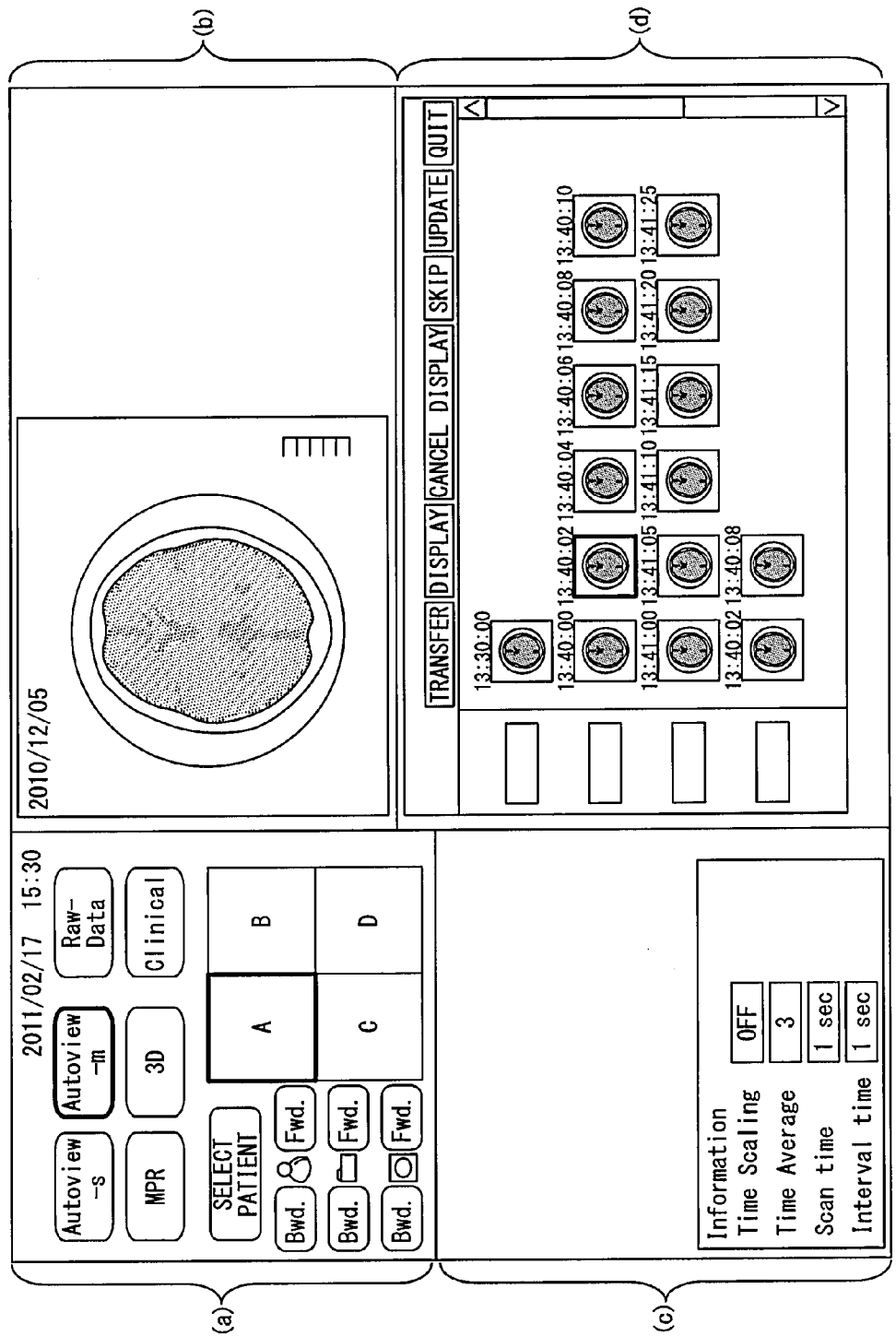
FIG. 9 is an explanation diagram illustrating another exemplary confirmation screen including bound stacks.

FIG. 9 is an explanation diagram illustrating another exemplary confirmation screen including bound stacks.

In step S203, the image binding unit 107 generates a bound stack made of a plurality of stacks having the same scan conditions and consecutive scan times and displays the generated bound stack in the area (d) (see FIG. 9). Binding a plurality of stacks reduces noise in an image itself and results in a clear image of inflow and outflow in blood vessels, for example. FIG. 9 shows an example in which the tomogram data items at the second row are bound into one stack every three stacks starting from a top of the data items and the bound stacks are displayed at the fourth row (bottom row).

Figure 10:
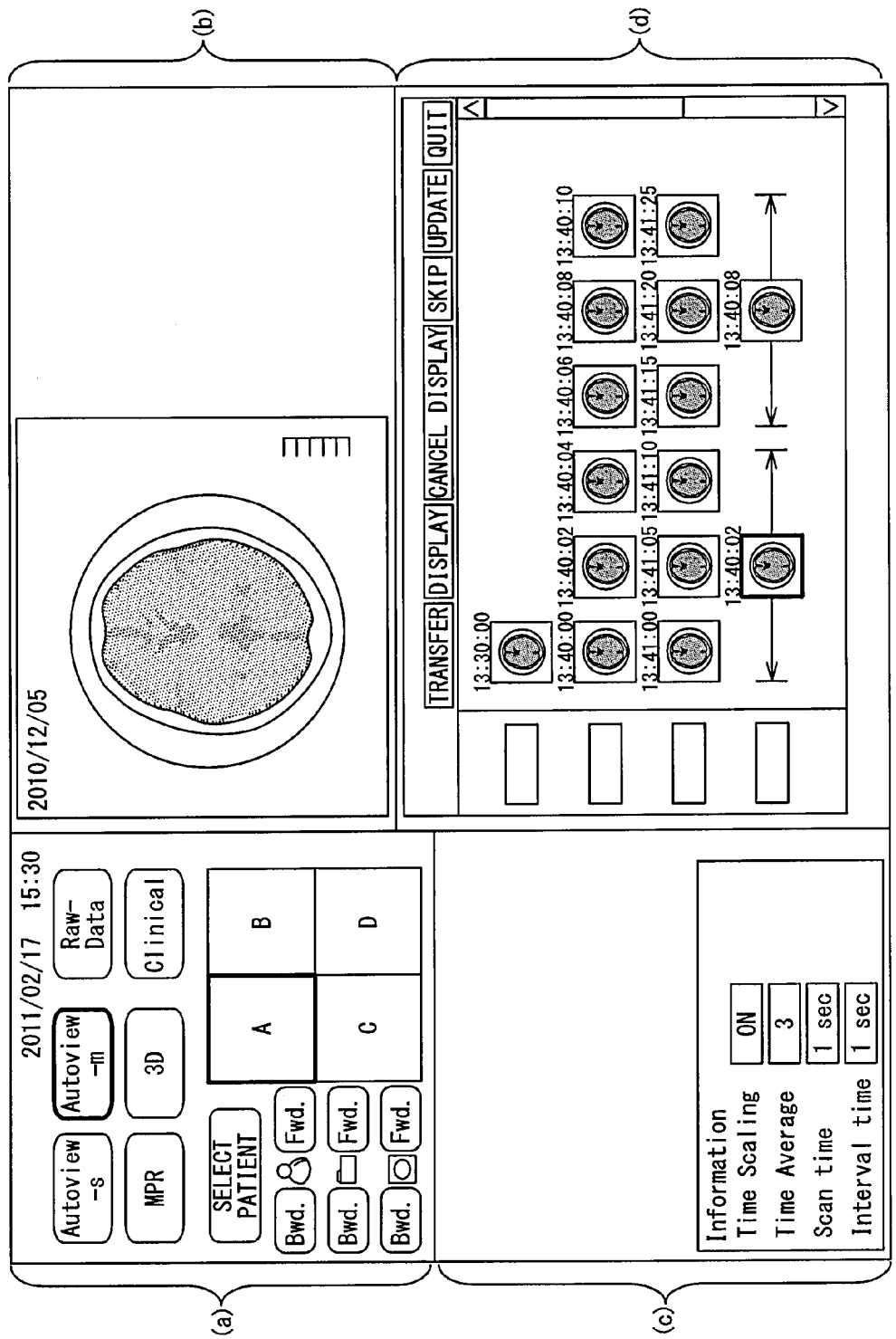
FIG. 10 is an explanation diagram illustrating another exemplary confirmation screen including time-scale display of the bound stacks.

FIG. 10 is an explanation diagram illustrating another exemplary confirmation screen including time-scale display of the bound stacks.

In step S205, the display switching unit 108 displays a bound stack obtained by binding the tomogram data items in the area (d) with a time-scale (see FIG. 10).

Similarly to FIG. 9, the fourth row in the area (d) of FIG. 10 shows an example of the case in which the tomogram data items at the second row are bound into one stack every three stacks starting from a top of the data items. Each stack at the fourth row in the area (d) of FIG. 10 is a bound stack in which pieces of time information of three stacks configuring each bound stack are added together. The display switching unit 108 performs time-scale display on the basis of the time information of the plurality of stacks configuring the bound stack. At this time, in detailed information on the scan in the area (c), time-scale display is "ON." Also, the display switching unit 108 may switch between presence and absence of the time-scale display and display a current state on the confirmation screen.

The tomogram data at the fourth row in the area (d) indicates that corresponding three stacks of the tomogram data at the second row are bound, and includes three-stack time information. According to the time-scale display, a time period corresponding to bound tomogram data is displayed under the tomogram data at the second row, and thereby the operator can visually confirm stacked images and a time range of images on the area (d).

It should be noted that a bound stack and a time-scale of the bound stack may be displayed at the bottom row as shown in the areas (d) of FIG. 9 and FIG. 10, or may be displayed at an upper or a lower row adjacent to a row at which a plurality of stacks configuring the bound stack are displayed. For example, assume that a plurality of stacks at the second row are bound to generate a bound stack. In this case, this bound stack may be displayed at the third row immediately under the second row, and tomogram data items originally at the third or later rows may be each moved down by one row. Alternately, this bound stack may be displayed at the second row, and tomogram data items originally at the second or later rows may be each moved down by one row.

According to the foregoing procedure, a bound stack obtained by binding a plurality of stacks may be displayed with a time-scale without using scan sequence information.

The X-ray CT apparatus 100 according to the second embodiment can display a bound stack obtained by binding a plurality of stacks with a time-scale without using scan sequence information. The user may view the time-scale display of the bound stacks (see the area (d) in FIG. 10), thereby easily confirming time information on the bound stacks and easily confirming a relationship between the bound stack and a plurality of stacks configuring the bound stack.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image display apparatus, comprising:
   a control circuit configured to obtain information on a scan sequence and obtain a plurality of scan time information values, each of the plurality of scan time information values being information of a time when scan data for each of a corresponding plurality of reconstructed medical images were picked up in accordance with the scan sequence;
   a memory configured to store the plurality of scan time information values obtained by the time information obtaining unit in association with the corresponding plurality of reconstructed medical images; and
   a display configured to simultaneously display the plurality of reconstructed medical images, each of which is associated with the corresponding scan time information value of the plurality of scan time information values stored in the memory, and a time chart indicating the scan sequence,
   wherein the control circuit is further configured to, when a reconstructed medical image of the plurality of reconstructed medical images displayed on the display is selected, display a marker indicating a time position on the time chart corresponding to a scan time information value associated with the selected reconstructed medical image.

2. The medical image display apparatus according to claim 1, wherein the control circuit is further configured to
   set a scan condition under which an image of an object is picked up; and
   create the scan sequence under the scan condition set by the scan condition setting unit as a time chart of changes in dose in a scan.

3. The medical image display apparatus according to claim 2, wherein
   the control circuit is further configured to, based on the set scan condition, collect the scan data of the object in accordance with the created scan sequence and create a corresponding plurality of reconstructed slice tomogram data, obtain information on the created time chart and obtain the plurality of scan time information values corresponding to the created plurality of reconstructed slice tomogram data, the memory is configured to store the plurality of scan time information values obtained by the time information obtaining unit in association with the plurality of reconstructed slice tomogram data, the display is configured to simultaneously display the plurality of reconstructed slice tomogram data, each of which is associated with the corresponding scan time information value stored in the memory and the created time chart, and the control circuit is further configured to, when reconstructed slice tomogram data of the plurality of reconstructed slice tomogram data displayed on the display is selected, display an image indicating a time position on the time chart corresponding to a scan time information value associated with the selected reconstructed slice tomogram data.

4. The medical image display apparatus according to claim 3, wherein when there is a body movement of the object in a scan, the control circuit does not create reconstructed slice tomogram data in the scan, and the control circuit is configured to indicate a corresponding position on the time chart at which the control circuit does not create the reconstructed slice tomogram data.

5. The medical image display apparatus according to claim 1, wherein the control circuit is further configured to generate a bound stack made by binding the plurality of reconstructed medical images having a same scan condition and consecutive scan times into one stack.

6. The medical image display apparatus according to claim 5, wherein when displaying the bound stack, the display is configured to, based on the plurality of scan time information values, perform time-scale display in which the bound stack is displayed with an image indicating a period during which the plurality of reconstructed medical images configuring the bound stack were picked up.

7. The medical image display apparatus according to claim 6, wherein the control circuit is further configured to switch between ON and OFF of the time-scale display in the display.

8. A medical image display apparatus, comprising:

a control circuit configured to obtain scan time information as information of a time when a medical image was picked up;

a memory configured to store the scan time information obtained by the control circuit in association with the medical image, wherein the control circuit is further configured to generate a bound stack made by binding a plurality of medical images having a same scan condition and consecutive scan times into one stack; and a display configured to display the medical image being associated with the scan time information stored in the memory, and configured to, when a bound stack bound by the control circuit is displayed, based on the scan time information, perform time-scale display in which the bound stack is displayed with a marker indicating a period from a time when a medical image picked up at first out of the plurality of medical images configuring the bound stack to a time when a medical image picked up last out of the plurality of medical images configuring the bound stack.

9. The medical image display apparatus according to claim 8, wherein the control circuit is further configured to switch between ON and OFF of the time-scale display in the display.

10. A non-transitory computer-readable medium storing a program causing a computer to perform the steps of:

obtaining information on a scan sequence and obtaining a plurality of scan time information values, each of the plurality of scan time information values being information of a time when scan data for each of a corresponding plurality of reconstructed medical images were picked up in accordance with the scan sequence;

associating the plurality of scan time information values with the corresponding plurality of reconstructed medical images;

displaying simultaneously, on a screen of a display, the plurality of reconstructed medical images, each of which is associated with the corresponding of scan time information value and a time chart indicating the scan sequence; and displaying, on the display, when a reconstructed medical image of the plurality of reconstructed medical images displayed on the display is selected, a marker indicating a time position on the time chart corresponding to a scan time information value associated with the selected reconstructed medical image.

11. A non-transitory computer-readable medium storing a program causing a computer to perform the steps of:

obtaining scan time information as information of a time when a medical image was picked up;

associating the scan time information with the medical image;

generating a bound stack made by binding a plurality of medical images having a same scan condition and consecutive scan times into one stack;

displaying the medical image associated with the scan time information on a display; and performing, when the bound stack is displayed on the display, based on the scan time information, time-scale display in which the bound stack is displayed with a marker indicating a period from a time when a medical image picked up at first out of the plurality of medical images configuring the bound stack to a time when a medical image picked up last out of the plurality of medical images configuring the bound stack.

\* \* \* \* \*